United States Patent
Hall et al.

(10) Patent No.: US 7,286,869 B2
(45) Date of Patent: *Oct. 23, 2007

(54) CHOICE OF WAVELENGTHS FOR MULTIWAVELENGTH OPTICAL IMAGING

(75) Inventors: David Jonathan Hall, Montréal (CA); Mathias Kohl-Bareis, Sinzig (DE)

(73) Assignee: ART, Advanced Research Technologies, Inc., Saint-Laurent, Quebec (CA)

( * ) Notice: Subject to any disclaimer, the term of this patent is extended or adjusted under 35 U.S.C. 154(b) by 417 days.

This patent is subject to a terminal disclaimer.

(21) Appl. No.: 10/757,938

(22) Filed: Jan. 16, 2004

(65) Prior Publication Data

US 2005/0010113 A1    Jan. 13, 2005

Related U.S. Application Data

(63) Continuation-in-part of application No. PCT/CA03/00046, filed on Jan. 22, 2003, and a continuation-in-part of application No. PCT/CA02/01081, filed on Jul. 16, 2002, which is a continuation-in-part of application No. 09/985,436, filed on Nov. 2, 2001, now Pat. No. 6,694,159.

(60) Provisional application No. 60/305,092, filed on Jul. 16, 2001.

(51) Int. Cl.
*A61B 5/00* (2006.01)
(52) U.S. Cl. ............... 600/473; 600/310; 600/323; 250/252.1
(58) Field of Classification Search ............ 600/310, 600/322, 323, 473, 475, 476, 477; 250/252.1, 250/363.02; 700/28
See application file for complete search history.

(56) References Cited

U.S. PATENT DOCUMENTS

| 4,945,239 | A | | 7/1990 | Wist et al. ............... 250/358.1 |
| 5,371,368 | A | | 12/1994 | Alfano et al. ............ 250/341.1 |
| 5,435,309 | A | * | 7/1995 | Thomas et al. ............ 600/310 |
| 6,223,133 | B1 | * | 4/2001 | Brown ......................... 702/28 |
| 6,341,257 | B1 | * | 1/2002 | Haaland ...................... 702/27 |
| 6,694,159 | B2 | * | 2/2004 | Hall et al. .................. 600/310 |

FOREIGN PATENT DOCUMENTS

WO    WO 03/007809    7/2002

OTHER PUBLICATIONS

Dam, Jan S. et al., *Fiber-Optic Probe for Noninvasive Real-time Determination of Tissue Optical Properties at multiple Wavelengths*, Applied Optics, Mar. 1, 2001, vol. 40, No. 7, pp. 1155-1164.
Zhou, Rulxia, *A Multiple Wavelength Algorithm in Color Image Analysis and Its Applications in Stain Decomposition in Microscopy Images*, Medical Physics, vol. 23, No. 12, Dec. 1996.
McBride, Troy O. et al., *Spectroscopic Diffuse Optical Tomography for the Quantitatiev Assessment of Hemoglobin Concentratino and Oxygen Saturation ni Breast Tissue*, Applied Optics, vol. 38, No. 25, Sep. 1, 1999.
Adamov, S.A. et al., *Spectrophotometric Quantitative Analysis of the Main Hemoglobin Derivatives*, Biochemistry (Moscow) Vo. 63, No. 10, 1998.

* cited by examiner

*Primary Examiner*—Eric F. Winakur
(74) *Attorney, Agent, or Firm*—Bereskin and Parr

(57) ABSTRACT

The present invention relates to a method for wavelength selection in a multi-wavelength TPSF or CW-based optical imaging system. This consists of identifying several chromophores in a highly turbid medium and selecting optimized wavelengths whereby using these wavelengths optimizes the deduction of the chromophore concentrations. Such chromophore concentrations may be combined to deduce other properties of the turbid medium.

22 Claims, 7 Drawing Sheets

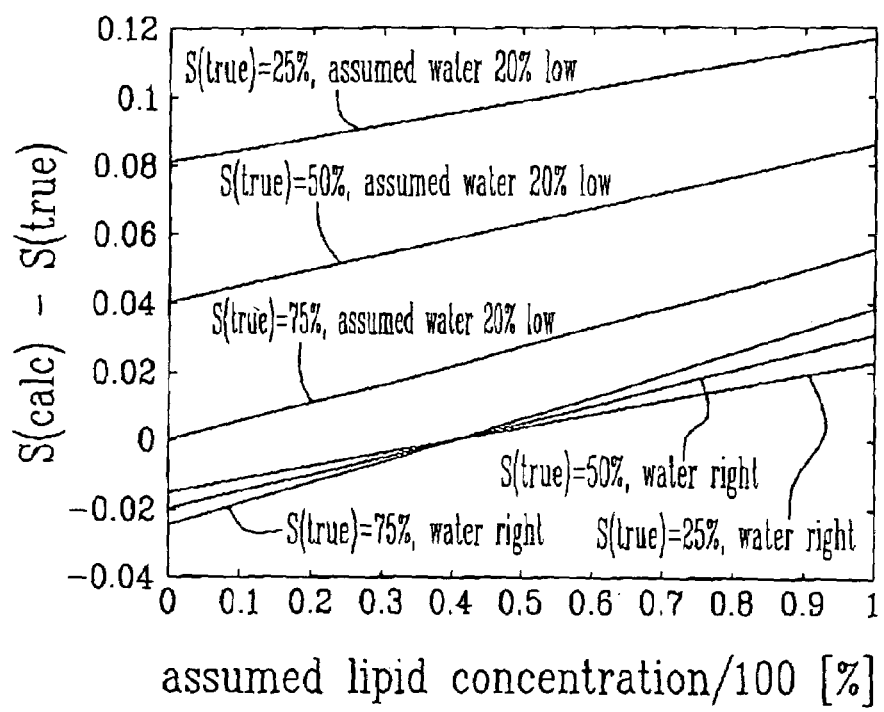

CHOICE OF WAVELENGTHS FOR MULTIWAVELENGTH OPTICAL IMAGING

CROSS-REFERENCE TO RELATED APPLICATIONS

This application is a Continuation-In-Part Application of PCT/CA02/01081, filed Jul. 16, 2002, designating the United States, now pending. This application is also a Continuation-In-Part of U.S. patent application Ser. No. 09/985,436, filed Nov. 2, 2001, now U.S. Pat. No. 6,694,159 now pending. This application claims priority under 35 U.S.C. 119(e) of U.S. Provisional Patent Application Ser. No. 60/305,092 filed Jul. 16, 2001. This application is also a Continuation in part of PCT/CA03/00046, filed Jan. 22, 2003, designating the United States, now pending. The specifications of said applications are hereby incorporated by reference.

MICROFICHE APPENDIX

Not applicable.

FIELD OF THE INVENTION

The present invention relates to the field of optical imaging in which objects which diffuse light, such as some human body tissues, are imaged using signals resulting from the injection of light into the object and detection of the diffusion of the light in the object at a number of positions. More particularly, the present invention relates to the choice of wavelengths for multiwavelength optical imaging in order to provide enhanced information.

BACKGROUND OF THE INVENTION

Optical medical imaging modalities such as Time-Domain and Continuous Wave show great promise as techniques for imaging breast tissue, as well as the brain and other body parts. In TD, the objective is to analyze the temporal point spread function (TPSF) of an injected pulse of light as it is diffused in the tissue. With CW, the attenuation of a continuous light source is measured. The information extracted from the TPSF and the attenuation signal is used in constructing medically useful images.

For example, one can extract time-gated attenuation information from the TPSF which provides high quality images albeit of lower resolution than other modalities such as X-ray imaging. Thus, it is unclear whether the spatial resolution provided by optical imaging is adeuate for diagnosing breast cancer based on morphology.

CW and TPSF data, when processed adequately, can be used to extract absorption values from raw measurements. For example, the TPSF can be used to decouple the light attenuation into absorption and scattering components. This extra information may be clinically useful. Moreover, one can obtain the tissue absorption spectrum by performing time-domain measurements at multiple wavelengths. In tissue there are several molecules which absorb the light and are known as chromophores. Spectroscopic analysis of the tissue absorption spectrum permits chromophore concentrations to be measured. Furthermore, combination of the chromophore concentrations can yield physiological information, as opposed to morphologic information, which could provide a more medically useful image.

The problem is one of knowing which are the dominant chromophores to include in a tissue model and then choosing the "best" wavelengths to deduce their concentrations most accurately.

SUMMARY OF THE INVENTION

It is an object of the invention to improve image quality in TPSF or CW-based optical images by choosing an efficient combination of wavelengths and combining information from the combination of wavelengths.

It is an object of the present invention to provide an objective method for choosing the wavelengths for a multiwavelength TPSF or CW-based optical imaging approach. For a given set of chromophores, the best selection of the wavelengths is performed for the set as a whole as opposed to choosing the best wavelength for each chromophore individually. Furthermore, hardware constraints can be taken into consideration in order to optimize the selection of wavelengths for a given device.

BRIEF DESCRIPTION OF THE DRAWINGS

Further features and advantages of the present invention will become apparent from the following detailed description, taken in combination with the appended drawings, in which:

FIG. 4 illustrates the deviation of calculated saturation and true saturation (S(calc)–S(true)) for a model tissue containing 15 µM [HbT], S(true)=25%, 50% and 75% and a lipid concentration of 40%. Two wavelengths at 760 and 850 nm were used to fit [oxy-Hb] and [deoxy-Hb]. The sensitivity with respect to wrong assumptions of lipid and water concentrations are shown;

It will be noted that throughout the appended drawings, like features are identified by like reference numerals.

DETAILED DESCRIPTION OF THE INVENTION

In accordance with the present invention, there is provided a method for selecting wavelengths for multiwavelength optical imaging.

Tissue Chromophores

Figure 1:
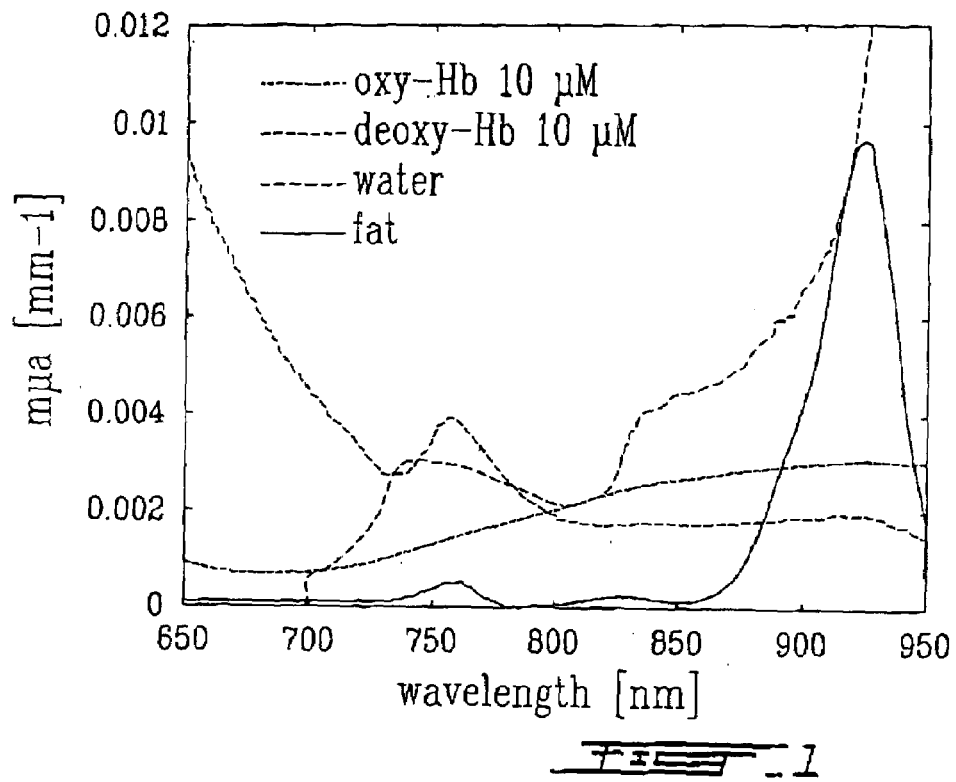
FIG. 1 illustrates the absorption spectra used of oxy-Hb, deoxy-Hb, pure water and lipid.

The dominant near infrared chromophores contained in breast tissue are considered to be hemoglobin (Hb) in its oxygenated (oxy-Hb) and deoxygenated (deoxy-Hb) forms, water and lipids. FIG. 1 shows the absorption spectra of oxy-Hb (at 10 μM concentration), deoxy-Hb (at 10 μM concentration), pure water (100% concentration), lipid (absorption spectrum of olive oil has been used to estimate the absorption spectrum of fat). There are other interesting near infrared chromophores, such as glucose and cytochrome c oxidase, but their absorption contribution in the breast is considered negligible compared to the aforementioned chromophores.

Physiological Information

Potentially useful physiological information about the breast tissue can be obtained from concentrations,[ ], of the chromophores. The total hemoglobin concentration, [HbT], defined as [HbT]=[oxy-Hb]+[deoxy-Hb], is related to the local vascular density. Since cancer is commonly associated with an increase in vascularisation (angiogenesis), a measurement of [HbT] could be medically useful. The fraction of hemoglobin that binds to oxygen is known as the oxygen saturation, S, and defined as S=[oxy-Hb]/[HbT]. Increased metabolic activity increases oxygen demands which decreases the oxygen saturation. Since cancer is commonly associated with increased metabolic activity, a measurement of S could also be medically useful.

Wavelength Choice

Historically as the biomedical optics field evolved the wavelengths were chosen for each chromophore individually by observing strong near infrared spectral features for the given chromophore and using the closest hardware-available wavelength. Many researchers also used the isobestic wavelength of oxy-Hb and deoxy-Hb, the wavelength where their absorption per concentration are equal, since this wavelength is insensitive to the oxygenation state of the hemoglobin and can be related to the (HbT).

However, the question both posed and addressed here is that for a given set of chromophores what are the optimal wavelengths to use in order to deduce the concentration of each chromophore? It is interesting to note that the isobestic wavelength used by many researchers turns out not to be one of the wavelengths of choice.

It is an object of the present invention to provide an objective method for choosing the wavelengths for a multiwavelength TPSF or CW-based optical imaging approach. For a given set of chromophores, the best selection of the wavelengths is performed for the set as a whole as opposed to choosing the best wavelength for each chromophore individually. Moreover, it is also possible to investigate scenarios such as the influence on determining chromophore concentrations under certain assumptions about the concentrations of other chromophore(s) in the set. Furthermore, hardware constraints can also be taken into consideration in order to optimize the selection of wavelengths for a given device. Fortunately, the recent advent of turn-key, pulsed, tunable near infrared wavelength lasers has permitted more viable availability of near infrared wavelengths.

Experimental Brute Force Approach

One possible approach to optimize the choice of wavelengths for a given set of chromophores is to conduct a brute force experimental study. This would consist of performing numerous experiments where different combinations of wavelengths are evaluated for the given set of chromophores at known concentrations until the optimum combination for deducing their concentrations is found. Obviously, this approach is likely to be highly time-consuming and it is not always trivial to provide a set of chromophores at known concentrations, particularly in the case of in vivo breast tissue.

Matrix Inversion Sensitivity Approach

An alternative approach which avoids the numerous experiments of the experimental brute force approach is a matrix inversion sensitivity approach. While the following example of an embodiment of the invention will be described with reference to TPSF-based parameters, it will be appreciated that by those skilled in the art that the example can be adapted to CW parameters as will be further explained below.

The equation which needs to be solved can be written for each wavelength as:

$$\mu_a(\lambda_1) = \sum_i m_{a,i}(\lambda_1) \cdot c_i$$

$$\mu_a(\lambda_2) = \sum_i m_{a,i}(\lambda_2) \cdot c_i$$

$$\ldots$$

$$\mu_a(\lambda_3) = \sum_i m_{a,i}(\lambda_3) \cdot c_i$$

where $\mu a$ is the measured absorption coefficient, $ma$ is the specific absorption coefficient of the different chromophores and $ci$ is the corresponding concentration.

This is written is matrix form as:

$$\mu_a = M \cdot c$$

where printing in bold indicates a matrix or vector. $\mu_a$ is a vector with a number of rows corresponding to the number of wavelengths ($n_\lambda$). c is a vector with the number of rows corresponding to the number of chromophores ($n_c$). M is a rectangular matrix of size $n_\lambda \times n_c$.

If $n_\lambda = n_c$ the system can be solved by matrix inversion $c = M^{-1}\mu_a$ and if $n_\lambda > n_c$ the system is overdetermined and can be solved by the pseudo-inverse $M^+ = (M^T M)^{-1} M^T$ where $M^T$ is the transposed matrix of M.

$$c = (M^+) \mu_a$$

The pseudoinverse $M^+$ is an $n_\lambda \times n_c$ array which is unique. If M is square (i.e. not overdetermined) the $M^+ = M^{-1}$. For given (i.e. chosen) wavelengths the pseudoinverse $M^+$ can be precalculated once and the matrix inversion corresponds to a simple matrix multiplication. This is the basis for the calculation of chromophore concentration.

One means to quantify the expected sensitivity of a matrix inversion of a matrix M with respect to small errors in the data is the condition number C which is defined as:

$$C = norm(M) \cdot norm(M^{-1})$$

C gives an indication of the accuracy of the results and is an estimate of the cross-talk between the different channels (i.e. chromophores concentrations). Values of C near 1 indicate a well-conditioned matrix, large values indicate an ill-conditioned matrix. The condition number is closely related to singular value decomposition (SVD) as it is the ratio of the largest and the smallest singular value of a matrix.

The matrix M for oxy-Hb and deoxy-HB at $\lambda = 760$ and 770 nm is $$M = \begin{matrix} 0.3871 & 0.1465 \\ 0.3280 & 0.1625 \end{matrix} \begin{matrix} \lambda = 760\,nm \\ \lambda = 770\,nm \end{matrix}$$

A matrix inversion is possible as the rank (M)=2, however the absorption at the two wavelengths is 'similar'. The condition number is C=20.49. Choosing the wavelengths to be $\lambda = 760$ and 850 nm gives the matrix $$M = \begin{matrix} 0.3871 & 0.1465 \\ 0.1729 & 0.2645 \end{matrix}$$

Inspection by eye already shows that the absorption is very 'different'. This is confirmed by the condition number: C=3.206. In what follows below the inverse of the condition number is plotted and analyzed. It has value between 0 and 1. 1/C close to 1 means 'orthogonal' spectra and low sensitivity to cross-talk. Small values of 1/C mean an ill-conditioned matrix. To find the best wavelengths, 1/C is calculated as a function of a wavelength. The wavelengths that give the highest values of 1/C are the best for a calculation of chromophore concentrations and the subsequent physiological information such as oxygen saturation, S.

Model absorption spectra were generated with the absorption spectra of FIG. 1 based on estimations of [HbT], S, lipid and water concentration. Matrix inversion based on different sets of wavelengths were performed to recover these parameters. These parameters were compared with the true ones for the different wavelengths and the sensitivity to noise or measurement offsets considered.

Assuming that we fit for the hemoglobin concentrations only and assuming certain values for water and lipid concentration, for a x-wavelengths matrix inversion, the best combination of wavelengths to give a well-conditioned matrix, the sensitivity of calculated values of oxy-Hb and deoxy-Hb concentration and oxygen saturation for variations of lipid or water concentration and sensitivity of S to measurement noise have been determined.

Figure 2:
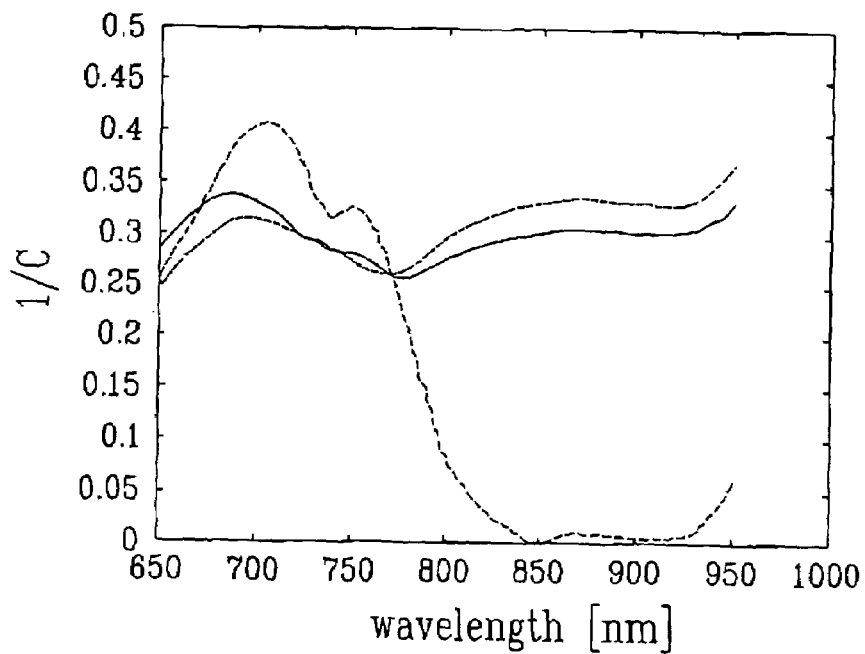
FIG. 2 illustrates the inverse of the condition number of the hemoglobin specific absorption matrix as a function of wavelength $\lambda 1$ being plotted for a system of a) two wavelengths. where the other wavelength is fixed at $\lambda 2=850$ nm, b) three wavelengths where the other wavelengths are fixed $\lambda 2=850$ nm and $\lambda 3=758$ nm and c) four wavelengths where the other wavelengths are fixed $\lambda 2=850$ nm, $\lambda 3=758$ nm and $\lambda 4=800$ nm.

In FIG. 2 the inverse of the condition number is shown for matrices of oxy-Hb and deoxy-Hb specific absorption coefficients for 2, 3 and 4 wavelengths. In each case one wavelength ($\lambda_1$) was varied between 650 and 950 nm while the remaining wavelengths were fixed $\lambda_2 = 850$ nm (2-wavelength system) $\lambda_2 = 850$ nm and $\lambda_3 = 758$ nm (3-wavelength system), and $\lambda_2 = 850$ nm, $\lambda_3 = 758$ nm and $\lambda_4 = 800$ nm (4-wavelength system). FIG. 2 indicates that the selection of two wavelength at $\lambda_1 = 850$ nm and $\lambda_2 = 700$ nm gives the highest values of 1/C and when the wavelength range is restricted via hardware constraints to >750 nm, a system that includes the peak wavelength of deoxy-Hb close to 760 nm is advantageous. It does not matter whether two or more wavelengths are used. This somewhat counterintuitive result is valid only without measurement noise and noise in the background absorption.

Figure 3:
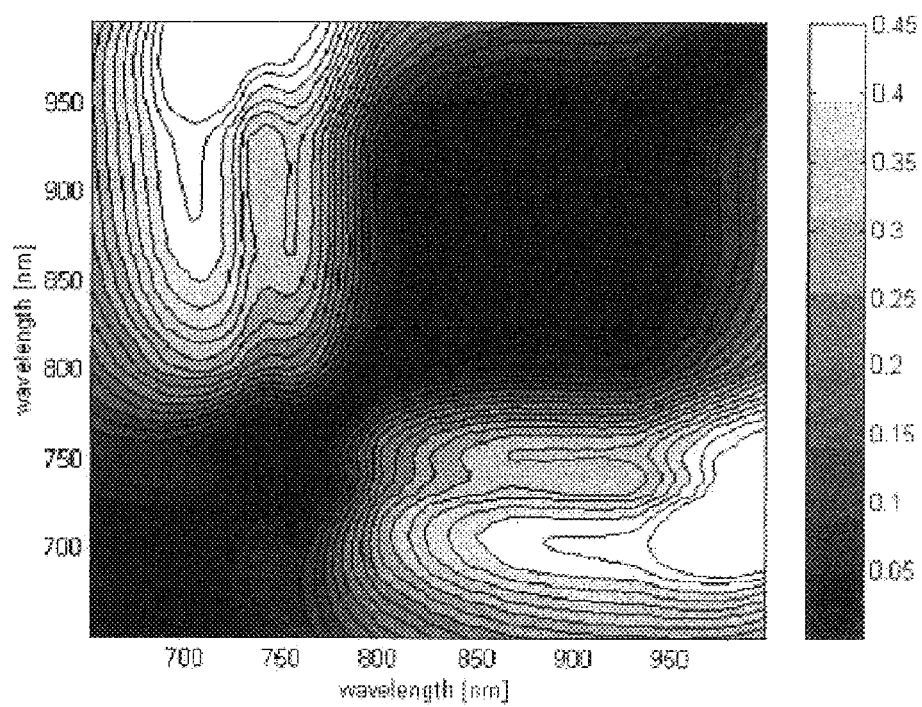
FIG. 3 illustrates the inverse of condition number C for the specific absorption spectra of oxy-Hb and deoxy-Hb as a function of $\lambda 1$ and $\lambda 2$. The plot is symmetric with respect to the diagonal. Regions of high values indicate combinations of wavelengths advantageous for spectroscopy.

FIG. 3 further highlights this finding for a two-wavelength matrix inversion. In this figure 1/C is plotted as a function of both at $\lambda_1$ and $\lambda_2$ in the range 650-950 nm. The plot is symmetric with respect to the diagonal. Regions of high 1/C-values can be chosen and the corresponding 'good' wavelengths can be read off the axis. It is apparent that (with the restriction to >750 nm) the one wavelength should be close to 760 nm while the other one can be within the range 830-900 nm without substantially affecting the condition number.

Using the spectra shown in FIG. 1, model tissue absorption spectra were generated. Based on matrix inversion values of [oxy-Hb], [deoxy-Hb] and S were backcalculated and the sensitivity to incorrect assumptions about the [water] and [lipid] tested. One approach is to take the measured $\mu_a$ spectra and subtract water and lipid absorption corresponding to certain assumed concentrations. For the data shown in FIG. 4, a model tissue containing 15 µM [HbT], (true)

saturation values of S=25%, 50% and 75% was used. Lipid concentration was 40%. It was tested how a misjudgement of water concentration affects the recalculated S value. To test the error in a simple two-wavelengths-fit (760 and 850 nm), the assumed lipid concentration was varied between 0 and 100%. When the assumed water concentration is right (lower three lines in FIG. 4), the deviation in saturation between true and calculated values is <±2% (obviously with zero error for the right lipid concentration of 40%). A misjudgement about the water concentration by 20% (upper lines in FIG. 5) results in additional errors in S(calc)−S(true) of up to 2% for S=75%, 4% for S=50% and 8% for S=25%. These errors in S are a function of the underlying tissue absorption coefficients. The values here give an indication about the order of magnitude.

Having a system with more than two fit-parameters, best wavelength combinations, for a three-components system of oxy-Hb, deoxy-Hb and lipid system, for a four-components system of oxy-Hb, deoxy-Hb, lipid and water, and the sensitivity of calculation of S to noise at the different wavelengths have been determined.

Figure 5A:
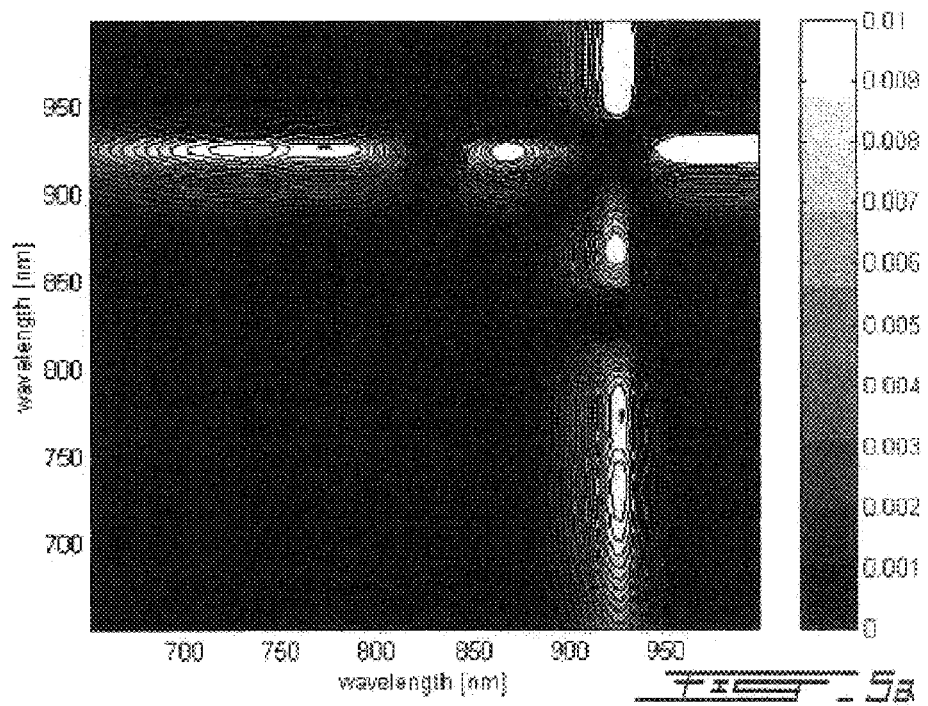
FIG. 5A illustrates the inverse of condition number C for the specific absorption spectra of oxy-Hb and deoxy-Hb and lipid for a fixed wavelength $\lambda 3=830$ nm as a function of $\lambda 1$ and $\lambda 2$. The islands of high values indicate advantageous wavelengths (scaling 0-0.01)
Figure 5B:
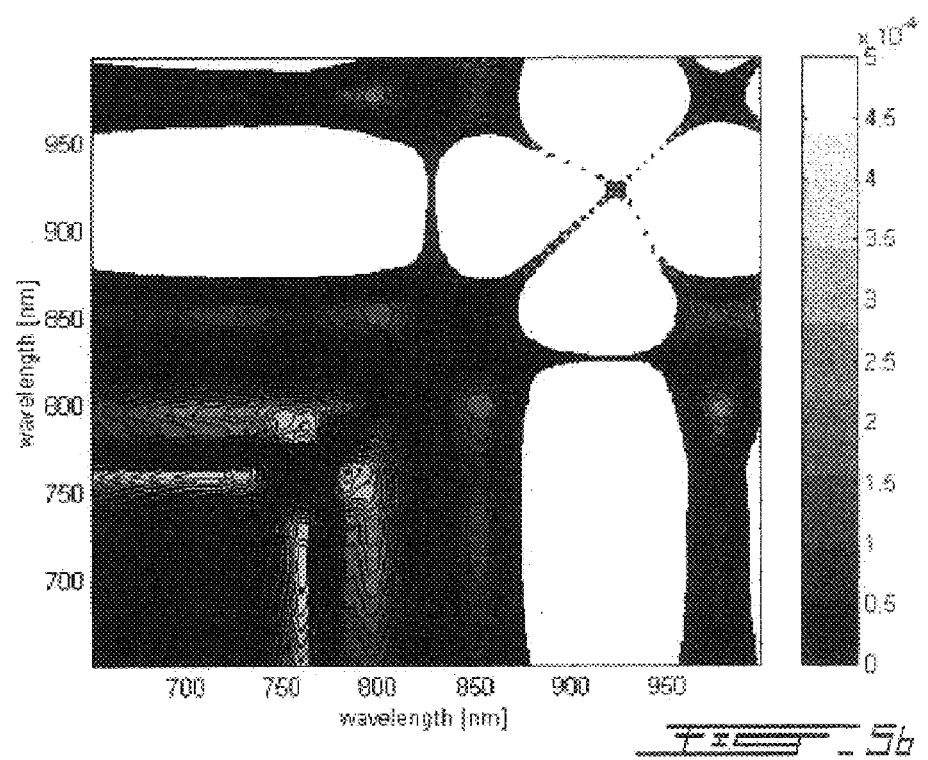
FIG. 5B illustrates the inverse of condition number C for the specific absorption spectra of oxy-Hb and deoxy-Hb and lipid for a fixed wavelength $\lambda 3=830$ nm as a function of $\lambda 1$ and $\lambda 2$ (same as FIG. 5A but scaling 0-0.0005)

In FIGS. 5A and 5B the inverse of the condition number is plotted for a three wavelengths system based on the oxy-Hb, deoxy-Hb and lipid specific absorption spectra as a function of $\lambda_1$ and $\lambda_2$. The third wavelength was fixed at $\lambda 3$=830 nm. Again, the plot is symmetric with respect to the diagonal. From FIG. 5A it is apparent, that there are three "islands" of high 1/C values. Unfortunately, all of these island would include wavelengths outside an imposed hardware constrained wavelength range of 750 to 850 nm. Plotting the same data in a different scale (FIG. 5B) shows that there is just a single preferential combination within this hardware constrained wavelength range: 760 and 780 nm.

Figure 6A:
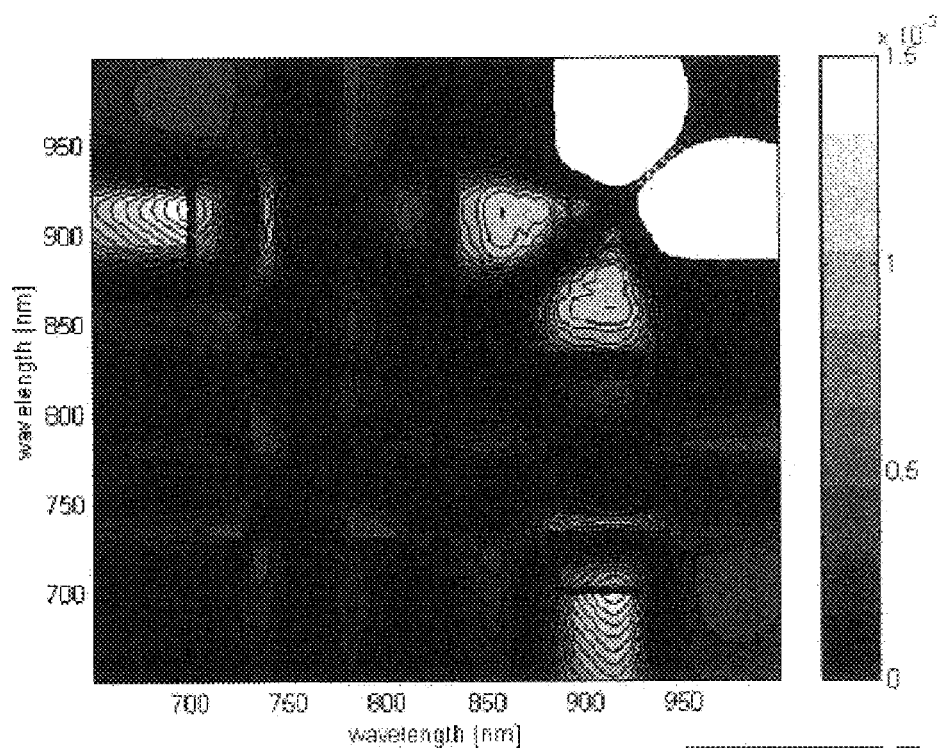
FIG. 6A illustrates the inverse of condition number C for the specific absorption spectra of oxy-Hb and deoxy-Hb, lipid and water for two fixed wavelength at $\lambda 3=760$ nm and $\lambda 4=830$ nm as function of $\lambda 1$ and $\lambda 2$ (scaling 0-0.0015). Regions of high values are advantageous for spectroscopy.
Figure 6B:
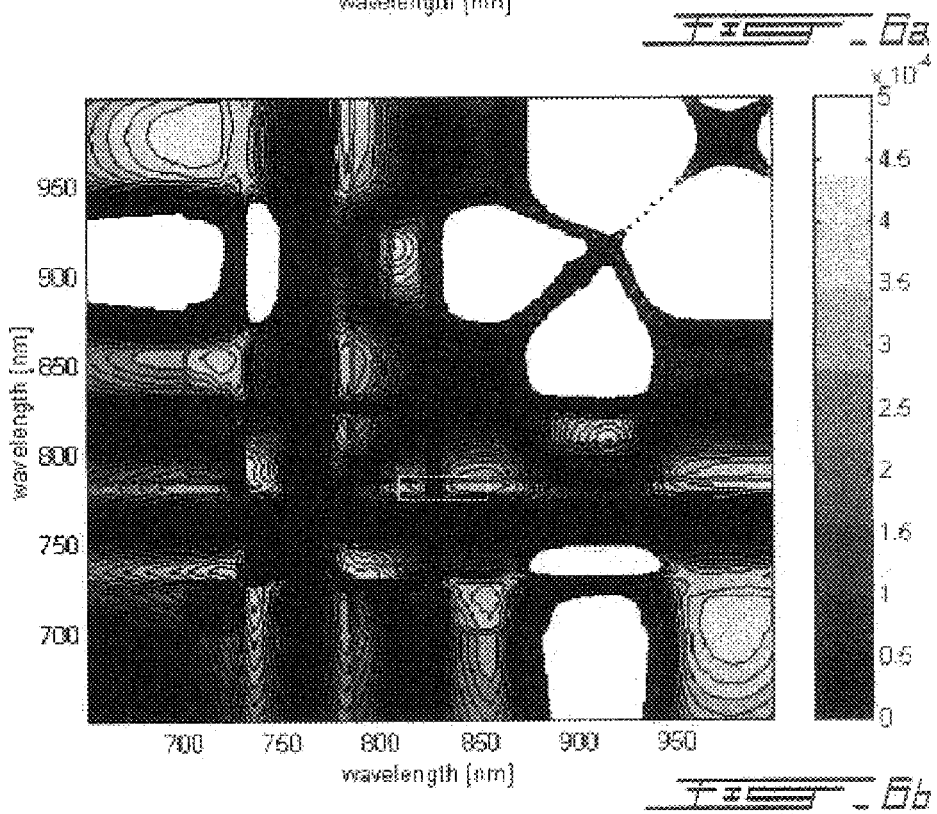
FIG. 6B illustrates the inverse of condition number C for the specific absorption spectra of oxy-Hb and deoxy-Hb, lipid and water for two fixed wavelength at λ3=760 nm and λ4=830 nm as function of λ1 and λ2. (same as FIG. 6A but scaling 0-0.0005)

Equivalent to FIGS. 5A and 5B, the inverse of C for a 4-wavelengths system is plotted in FIGS. 6A and 6B. Again, the difference between them is the scaling. Two wavelengths were fixed at $\lambda 3$=760 nm and $\lambda 4$=830 nm. Including the wavelengths outside the 750-850 nm range there appear four preferential combinations. Restricting the wavelength range to 750-850 nm there are just two advantageous region (marked by the white rectangle in FIG. 6B): 780 nm and 850 nm, and 780 nm and 815 nm.

From the analysis based on matrix condition numbers, the best wavelength combinations for 2, 3 and 4 wavelengths measurements are the following:

TABLE 1

Wavelength combinations for 2, 3 and 4 wavelengths measurements

| Wavelength | Best wavelengths (nm) | | | | | see |
|---|---|---|---|---|---|---|
| Range | λ1 | λ2 | λ3 | λ4 | fit for | FIG. |
| 2-λ 650–950 nm | 700 | >860 | | | Oxy-Hb, | 2, 3 |
| 750–850 nm | 760 | 850 | | | deoxy-Hb | |
| 3-λ 650–950 nm | 700–760 | 830 | 925 | | +lipid | 5A, |
| | 830 | 860–870 | 925 | | | B |
| 750–850 nm | 760 | 780 | 830 | | | |
| 4-λ 650–950 nm | 760 | 830 | 860 | 925 | +lipid, | 6A, |
| | 700 | 760 | 830 | 925 | +water | B |
| 750–850 nm | 760 | 780 | 830 | 850 | Best | |
| | 760 | 780 | 815 | 830 | combination | |

Furthermore, it must be pointed out that including more wavelengths does not increase the condition number. E.g. for the four chromophores and all wavelengths in the range 750-850 nm, 1/C=0.000314. This is lower than the value (1/C=0.00036, compare with FIG. 6B) when only four wavelengths (760, 760, 830 and 850 nm) are used. In a system without noise and no other chromophores than the four considered here, a 4-wavelengths system is the optimal.

Figure 7:
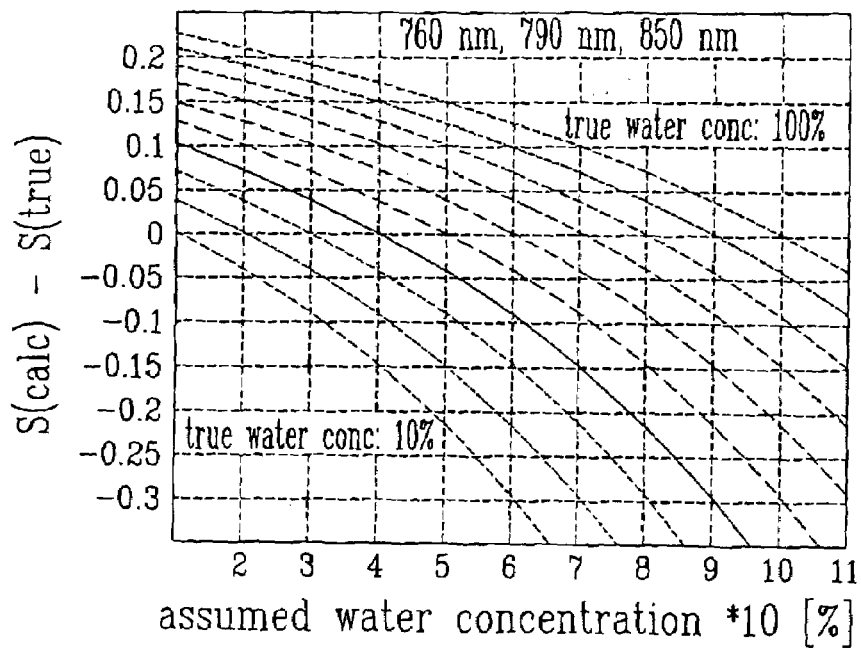
FIG. 7 illustrates the estimation of deviations from true saturation values for a model tissue of [HbT]=20 μM, S=75%, a lipid concentration of 40% and true water concentration corresponding to 0-100% water. Three wavelengths at 760, 780 and 850 nm were used for back calculation of S, shown here as a function of assumed water concentration.

While certainly only a 4-wavelengths measurement allows [oxy-Hb], [deoxy-Hb], [lipid] and [water] to be determined, and a 2-wavelengths system (see FIG. 5) is not sufficient, the question is posed whether a 3-wavelengths measurement might supply S values with a high enough precision. In this case the concentration of one chromophore (water or lipid) must be guessed and the corresponding absorption subtracted from the measured $\mu_a$ values. This was tested with a model absorption spectrum and is shown in FIG. 7 for 760, 780 and 850 nm. True water concentration was varied between 10 and 100% (the different lines), and the difference between calculated and true saturation values plotted as a function of assumed water concentration. For instance, for a true water concentration of 50%, a misjudgment of the water concentration by 10% results in an error in S by about 4%.

Up to now, only "perfect" data sets were considered with no noise. In real situations there are problems due to measurement noise that is random for the different wavelengths; unknown chromophores in the tissue, i.e. there is a background absorption coefficient the spectrum of which we do not know; and possible systematic errors in the primary $\mu_a$ recovery.

There are an ample number of parameters which can be considered and as examples the following two questions are considered. First, is the oxygen saturation more susceptible to noise at certain wavelengths? Second, what is the influence of an offset in the $\mu_a$ data?

The influence of errors (noise) in $\mu_a$ on the calculated Hb concentrations and saturation values was estimated in a model tissue based on 20 μM [HbT], S=50% and a lipid and water concentration of 30% and 40% respectively. Matrix inversion was performed on the $\mu_a$-spectrum of this model tissue for wavelengths 760, 780, 830 and 850 nm. The sensitivity to noise (i.e. variations in μa) at the different wavelengths was estimated by changing the absorption coefficient at a single wavelength by +0.0001 $mm^{-1}$. In FIG. 3, the change in calculated (oxy-Hb), [deoxy-Hb] and oxygen saturation value due to this "noise" is plotted. This figure shows that the change in oxygen saturation value is about −2% for changes at 760 nm, <0.5% at 780 nm, while it translates to a variation of +6% at 830 nm.

Figures 9A, 9B, 10A, 10B:
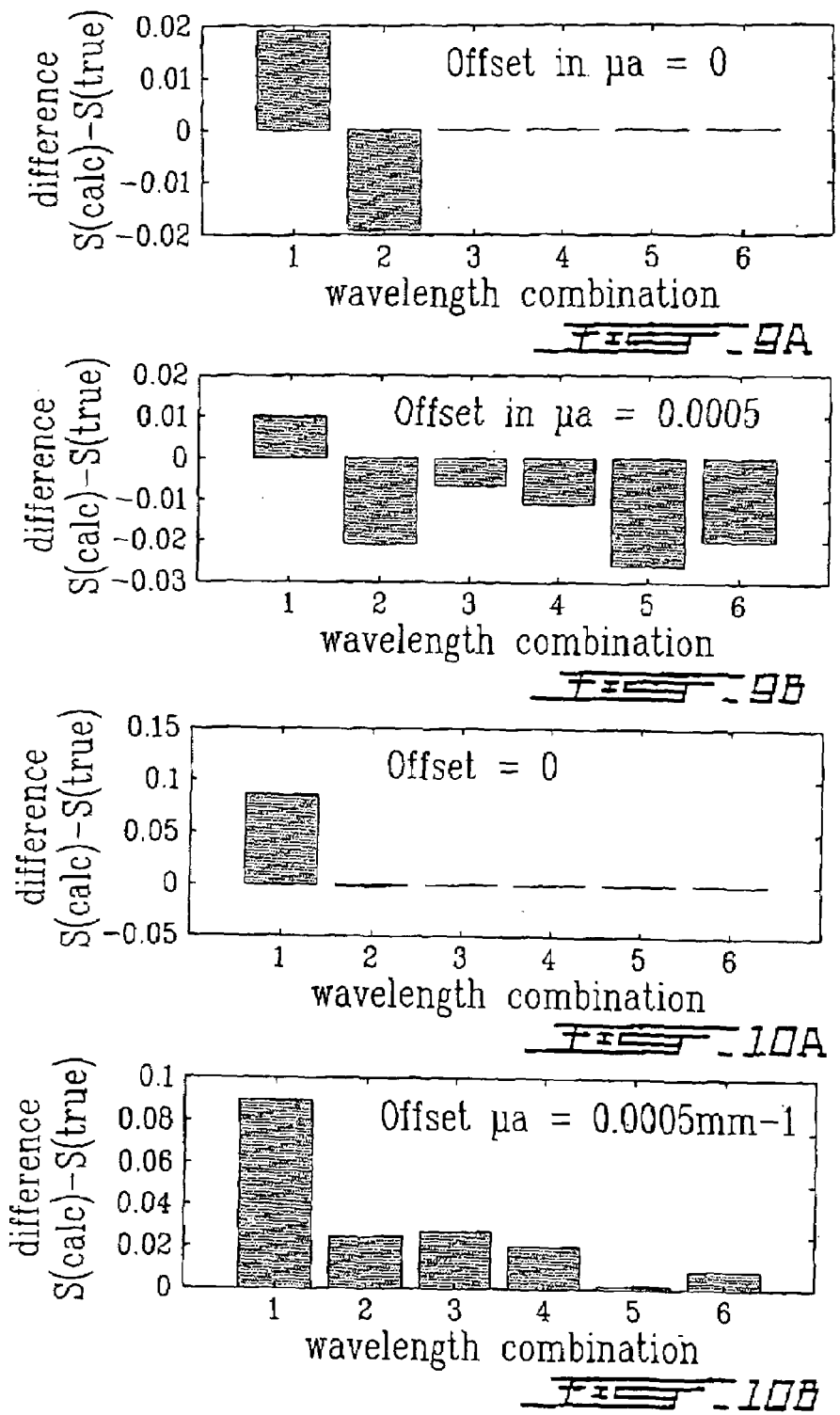
FIG. 9 illustrates the estimation of the recovery of saturation values based on different wavelength combinations. A model tissue of 20 μM [HbT], a true saturation of S=75%, lipid and water concentration of 40% were used. in the lower plot an offset of 0.0005 $mm^{-1}$ independent of wavelength was added to the model tissue μa-spectrum (no offset in the upper plot). Plotted are deviations of the saturation values due to matrix inversion and the true 75% value. The following wavelength combinations were used: 1) 760 nm and 850 nm, 2) 760, 830 and 850 nm, 3) 760, 780, 830 and 850 nm, 4) 750-850nm, 5) 720-850 nm, 6) 720-900 nm.
FIG. 10 illustrates the estimation of the recovery of saturation values based on different wavelength combinations. A model tissue of 20 μM [HbT], a true saturation of S=50%, lipid and water concentration of 40% were used in the lower plot an offset of 0.0005 $mm^{-1}$ independent of wavelength was added to the model tissue μa-spectrum (no offset in the upper plot). Plotted are deviations of the saturation values due to matrix inversion and the true 75% value. The following wavelength combinations were used: 1) 760 nm and 850 nm, 2) 760, 830 and 850 nm, 3) 760, 780, 830 and 850 nm, 4) 750-850 nm, 5) 720-850 nm, 6) 720-900 nm.

There are two conditions that produce an offset in the measured $\mu_s$-spectra with respect to the true values. First, the algorithm for $\mu_a$-calculation based on TPSF-based optical imaging might lead to a systematic offset e.g. due to residual crosstalk between absorption and scattering parameters. Second, the tissue absorption might have a background of unknown origin (chromophore). Under both conditions the fitting of $\mu_a$-data with the four chromophores is hampered. The effect of such an offset for different wavelength combinations is estimated with a model spectrum of 20 μM (HbT), S=75% and water and lipid concentration of 40%. An offset of 0.0005 $mm^{-1}$ was added to the $\mu_a$-values independent of wavelength. The effect on the calculated oxygen saturation values is known in FIG. 9 for combination of 2, 3 and 4 wavelengths as well as continuous spectra between 750-850, 720-850 and 720-900 nm. It is apparent that the lowest error in S is achieved by the 4-wavelengths combination. Including more wavelengths increases the error. In FIG. 10 the same calculation was done, however, for a true oxygen saturation value of 50%. Here the lowest error is achieved by the 720-850 nm wavelength range, while using less wavelengths or increasing the fitting range to 900 nm results in larger errors.

Figure 8A:
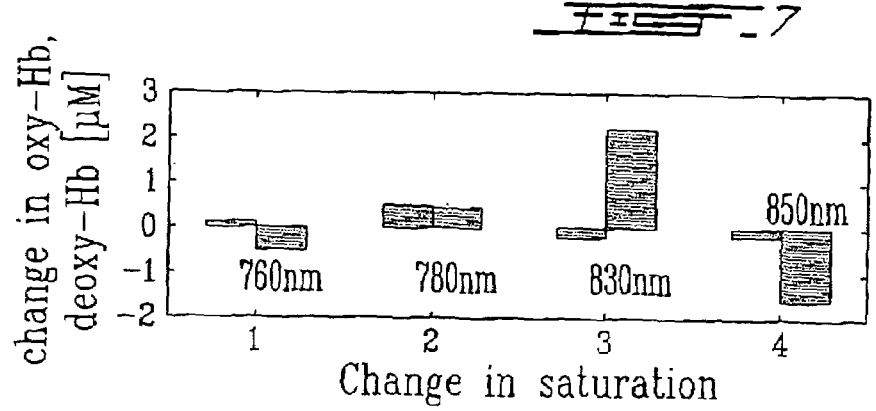
FIG. 8 illustrates the estimation of the influence of errors (noise) in $\mu_a$ on the calculated Hb concentrations and saturation values. A model $\mu_a$-spectrum based on 20 μM [HbT], S=50%, and a lipid and water concentration of 30% and 40% was assumed. Matrix inversion was performed for wavelengths 760, 790, 830 and 850 nm. plotted is the change in calculated [oxy-Hb], [deoxy-Hb] and saturation value when the $\mu_a$ value at a single wavelength was changed by +0.0001 $mm^{-1}$. This plot suggests that noise at 830 nm translates in the highest noise in saturation values.
Figure 8B:
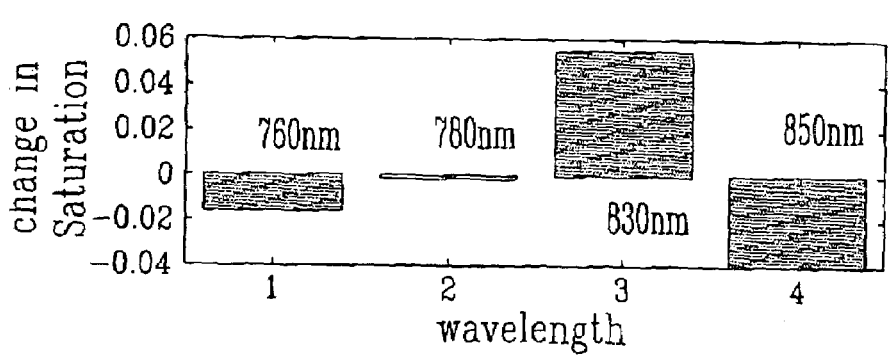

Based on the assumption that the dominant tissue chromophores are oxy-Hb, deoxy-Hb, water and lipid and analysis of the matrix condition number, measurements at the wavelengths 760, 780, 830 and 850 nm supply an optimal data set when the wavelength range is limited to 750-850 nm under ideal conditions. As shown in FIGS. 5 and 6, inclusion of shorter and longer wavelengths promise a better matrix inversion. Under real conditions there is no clear-cut answer about the improvement when more wavelengths are included (see FIGS. 9 and 10). It might be advantageous to reduce measurement noise at 4 wavelengths due to longer scan times rather than to include more wavelengths. As demonstrated in FIG. 8, to achieve an optimal accuracy the noise level at different wavelengths has to be adjusted which might require different measurement times at certain wavelengths.

Strictly speaking the work presented here was achieved by optimizing a 2-wavelength system and then optimizing a 4-wavelength system where 2 of the wavelengths were fixed at the optimized 2-wavelength system values. Whilst this is easier to display graphically, preferably all 4 wavelengths would be permitted to vary in a global optimization process. Fortunately, for the specific example presented here when all 4 wavelengths are permitted to vary the same optimal solution is found. However, this may not be true for all situations and a global optimization is preferred.

It will be appreciated that parameters of the system other than wavelengths can be optimized For example the light source type and source power, the detector type and detector aperture for each wavelengths, the choice of image algorithm, the source/detector geometries, the acquisition time and the noise characteristics are parameters that can be adjusted or chosen, as would be known to one skilled in the art, to optimize the determination of chromophores concentration and the optical image obtained therewith. In a preferred embodiment, optimization of the parameters is performed by taking in consideration the matrix inversion approach for optimizing wavelength selection as described above.

It is also understood that it will be obvious to those skilled in the art that the same approach for choosing optimal wavelengths can be applied to optical absorption spectroscopy in general. For example, in other embodiments of the present invention the method of the present invention is also used for choosing the optimal wavelengths for analyzing the components of paints, pharmaceutical products, food, grain or any other turbid media.

It is also understood that the proposed method applies both to the analysis of absolute chromophore concentrations as to their changes or relative concentrations.

It is also understood that the proposed method applies both to the analysis of absolute chromophore concentrations as to their changes or relative concentrations.

Further, it is also understood that the proposed method applies when continuous wave (CW) methods are used and an assumption for scattering is made, e.g. a constant value or following a scatter-power wavelength dependent law, in order to infer the absorption coefficient, rather than measuring the absorption coefficient directly with a TPSF-based approach.

Thus, changes in CW measurements can be converted into absorption changes $\Delta A(\lambda)$ which are then used to calculate changes in concentrations $\Delta c_i$ based on a modified Beer-Lambert law which assumes a predetermined wavelength dependence of the optical pathlength $D_9(\lambda)$ (Cope & Delpy, 1998; Essenpreis et al., 1992) to account for scattering.

$$\Delta A(\lambda) = \sum_i [m_{ai}(\lambda) \cdot \Delta c_i \cdot D_a(\lambda)]$$

Thus $\Delta c_i = N^{-1}\Delta A$, where N is similar to M but incorporates $D_9(\lambda)$, and is the matrix which is used for optimizing the choice of wavelengths.

Further, it is understood that the proposed method applies not only for a mixture of endogenous absorbers (chromophores), but also for mixtures of exogenous absorbers with known spectra, such as optical dyes or fluorophores, or for a mixture of both endogenous and exogenous absorbers.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The embodiment (s) of the invention described above is(are) intended to be exemplary only. The scope of the invention is therefore intended to be limited solely by the scope of the appended claims.

We claim:

1. A method of optical imaging of turbid media using a plurality of discrete wavelengths in an optical imaging system, the method comprising the steps of:
   selecting a set of chromophores for characterizing a property of the turbid media;
   defining parameters of the system including at least a number of said discrete wavelengths, a value of each of said wavelengths, source power and detector aperture for each of said wavelengths, a choice of image algorithm and source/detector geometries, a choice of source and detector and noise characteristics;
   fixing a value of all of said parameters except a plurality of said parameters values to be optimized;
   determining an optimal value for each of said parameter values to be optimized as a function of a performance of the system in measuring a concentration of said chromophores in said turbid media for characterizing said property as a whole; and
   using said optimal value for each of said parameter values in imaging said turbid media.

2. The method of claim 1 wherein said optical imaging system is selected from Time-Domain (TD) modality which generates Temporal Point Spread Functions (TPSF), and Continuous Wave (CW) modality.

3. The method of claim 2, wherein said imaging is medical imaging, said highly turbid medium being body tissue and said property is physiological.

4. The method of claim 3, wherein said parameter values to be optimized comprise a value of each of said wavelengths.

5. The method of claim 4, wherein said parameter values to be optimized further comprise said number of said discrete wavelengths.

6. The method of claim 5, wherein said step of determining comprises fixing said number of discrete wavelengths at each of a plurality of numbers, and determining an optimized performance of the system in measuring a concentration of said chromophores in said turbid media at each of said plurality of wavelengths, and selecting one of said plurality of numbers having a best optimized performance.

7. The method of claim 6, wherein said step of determining an optimal value for each of said parameters comprises minimizing a condition number of a matrix of specific absorption coefficients of said chromophores as a function of wavelength.

8. The method of claim 5, wherein said step of determining an optimal value for each of said parameters comprises minimizing a condition number of a matrix of specific absorption coefficients of said chromophores as a function of wavelength.

9. The method of claim 4, wherein said step of determining an optimal value for each of said parameters comprises minimizing a condition number of a matrix of specific absorption coefficients of said chromophores as a function of wavelength.

10. The method of claim 3, wherein said plurality of chromophores comprise at least oxy-hemoglobin and deoxy-hemoglobin.

11. The method of claim 10, wherein said chromophores are water, lipids, oxy-hemoglobin and deoxy-hemoglobin.

12. The method of claim 11, wherein said imaging system is TPSF-based and wherein values of said wavelengths are 760 nm, 780 nm, 830 nm and 850 nm.

13. The method of claim 10, wherein said body tissue is breast tissue.

14. The method of claim 10, wherein said optical imaging system is TPSF-based and wherein said number of wavelengths selected is from 2 to 4.

15. The method of claim 14, wherein said number is 4.

16. The method of claim 1, wherein said step of determining comprises empirically determining said performance of the system for a range of said values for each of said parameter values to be optimized.

17. The method of claim 1, wherein the step of determining an optimal value of said parameters to be optimized comprises:
deriving an inherent wavelength-dependent sensitivity to noise in calculating said chromophore concentrations, and
determining an optimal correlation of said sensitivity and at least one other of said parameters.

18. The method of claim 17, wherein said imaging system is TPSF-based and wherein one of said parameters to be optimized is a distribution of an acquisition time at each of said wavelengths.

19. The method of claim 1, wherein said imaging system is TPSF-based and wherein one of said parameters to be optimized is a distribution of an acquisition time at each of said wavelengths.

20. The method of claim 19, further comprising a step of determining a minimum value for said acquisition time at which said performance of said system attains a minimum threshold value.

21. The method of claim 1, wherein one of said parameters to be optimized is at least one of said source power and said detector aperture for each of said wavelengths.

22. The method of claim 21 wherein said imaging system is TPSF-based, further comprising a step of determining a minimum value for an acquisition time at which said performance of said system attains a minimum threshold value.

* * * * *